United States Patent [19]

Jarmas

[11] Patent Number: 5,693,857
[45] Date of Patent: Dec. 2, 1997

[54] PROCESS AND INTERMEDIATE FOR THE PREPARATION OF 2-HYDROXY-3-SULFIDO-3-PHENYL PROPANOIC ACIDS

[75] Inventor: Alvydas Alfonsas Jarmas, Wynnewood, Pa.

[73] Assignee: SmithKline Beecham Corporation, Philadelphia, Pa.

[21] Appl. No.: 428,925

[22] Filed: Apr. 24, 1995

Related U.S. Application Data

[63] Continuation of Ser. No. 975,556, filed as PCT/US91/05433, Jul. 31, 1991, abandoned, which is a continuation of Ser. No. 561,621, Aug. 1, 1990, abandoned.

[51] Int. Cl.$^6$ .................. C07C 315/00; C07C 317/00
[52] U.S. Cl. .......................... 562/429; 562/426
[58] Field of Search ........................ 562/426, 429

[56] References Cited

U.S. PATENT DOCUMENTS

| | | | |
|---|---|---|---|
| 4,655,189 | 4/1987 | Baker et al. | 96/136 |
| 4,665,189 | 5/1987 | Baker et al. | 548/252 |
| 4,820,719 | 4/1989 | Gleason et al. | 514/381 |
| 4,874,792 | 10/1989 | Gleason et al. | 514/570 |
| 5,110,959 | 5/1992 | Flisak et al. | 549/549 |

FOREIGN PATENT DOCUMENTS

| | | |
|---|---|---|
| 0 358 240 | 4/1986 | European Pat. Off. . |
| 0 296 732 | 12/1988 | European Pat. Off. . |
| 296732 | 12/1988 | European Pat. Off. . |
| 0 313 697 | 5/1989 | European Pat. Off. . |
| 0 365 249 | 9/1989 | European Pat. Off. . |

OTHER PUBLICATIONS

Gleason et al., *J. Med. Chem.*, 30, 959 (1987).
Chong, et al., *J. Org. Chem.*, 50, 1560 (1985).
Sharpless et al., *Pure Appli. Chem.*, 55, 589 (1983).
Liwschitz et al., *J. Chem. Soc.*, 1116 (1962).
Harada et al., *Bull. Chem. Soc. Jpn.*, 47, 2911 (1974).
Harada et al., *Bull. Chem. Soc. Jpn.*, 39, 2311 (1966).
Harada, *J. Org. Chem.*, 31, 1407 (1966).
Mohrig et al., *J. Org. Chem.*, 46, 4655 (1981).

*Primary Examiner*—Marianne M. Cintins
*Assistant Examiner*—Dwayne C. Jones
*Attorney, Agent, or Firm*—Charles M. Kinzig; Edward T. Lentz

[57] ABSTRACT

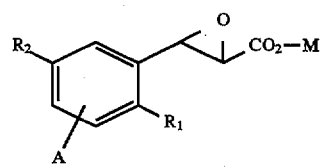

This invention relates to intermediate compounds of formula (VI), wherein: $R_1$ is $(L)_a$—$(CH_2)_b$—$(T)_c$—B; a is 0 or 1; b is 3 to 14; c is 0 or 1; L and T are independently sulfur, oxygen, CH=CH, C≡C, or $CH_2$; B is H, $C_{1-4}$alkyl, ethynyl, trifluoromethyl, isopropenyl, furanyl, thienyl, cyclohexyl or phenyl unsubstituted or monosubstituted by Br, Cl, $CF_3$, $C_{1-4}$alkoxy, $C_{1-4}$alkyl, methylthio or trifluoromethylthio; $R_2$ and A are independently selected from H, $CF_3$, $C_{1-4}$alkyl, $C_{1-4}$alkoxy, F, Cl, Br, I, OH, $NO_2$ or $NH_2$; or, when $R_1$ and A are H, $R_2$ is $(L)_a$—$(CH_2)_b$—$(T)_c$—B wherein a, b, c, L, T and B are as defined above; and M is H, Li, Na, K, $NH_4$ or an organic ammonium cation, and their use in a process for preparing leukotriene antagonists.

8 Claims, No Drawings

PROCESS AND INTERMEDIATE FOR THE PREPARATION OF 2-HYDROXY-3-SULFIDO-3-PHENYL PROPANOIC ACIDS

This is a Continuation of application Ser. No. 07/975,556, filed Feb. 1, 1993, abandoned on May 2, 1995 which is a continuation of PCT/US91/05,433 filed on Jul. 31, 1991, which is a continuation of Ser. No. 07/561,621 filed on Aug. 1, 1990, which was abandoned in Aug. 12, 1991.

FIELD OF THE INVENTION

This invention relates to a novel intermediate and a process for preparing pharmaceutically active agents.

BACKGROUND

Compounds of the general formula (I):

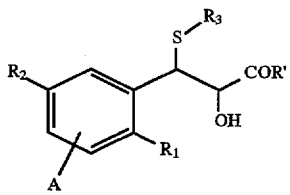

wherein:
$R_1$ is $(L)_a$—$(CH_2)_b$—$(T)_c$—B;
a is 0 or 1;
b is 3 to 14;
c is 0 or 1;
L and T are independently sulfur, oxygen, CH=CH, C≡C, or $CH_2$;
B is H, $C_{1-4}$alkyl, ethynyl, trifluoromethyl, isopropenyl, furanyl, thienyl, cyclohexyl or phenyl unsubstituted or monosubstituted by Br, Cl, $CF_3$, $C_{1-4}$alkoxy, $C_{1-4}$alkyl, methylthio or trifluoromethylthio;
R' is OH, $NH_2$, aryloxy or $C_{1-6}$alkoxy;
$R_2$ and A are independently selected from H, $CF_3$, $C_{1-4}$alkyl, $C_{1-4}$alkoxy, F, Cl, Br, I, OH, $NO_2$ or $NH_2$; or, when $R_1$ and A are H, $R_2$ is $(L)_a$—$(CH_2)_b$—$(T)_c$—B wherein a, b, c, L, T and B are as defined above;
$R_3$ is $(CH_2)_n CH(R_5)COR_6$, $CH(CO_2H)CH_2CO_2H$, $CH_2CH_2Z$,

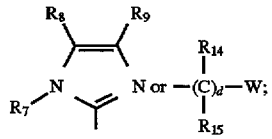

n is 0 to 6;
$R_5$ is hydrogen, amino, or $NHCOCH_2CH_2CH(NH_2)CO_2H$;
$R_6$ is hydroxy, amino, $NHCH_2CO_2H$ or $C_{1-6}$alkoxy;
Z is $SO_3H$, $SO_2NH_2$ or CN;
$R_7$ is hydrogen, $C_{1-4}$alkyl or $C_{3-4}$alkenyl;
$R_8$ is hydrogen, $C_{1-4}$alkyl, carboxyl, carboxamido, or $(CH_2)_pCO_2R_{12}$, wherein p is 1 or 2 and R12 is $C_{1-6}$alkyl or hydrogen when $R_7$ and $R_9$ are hydrogen or $C_{1-4}$alkyl;
$R_9$ is hydrogen, $C_{1-4}$alkyl, or $(CH_2)_pCO_2R_{13}$, wherein p is 1 or 2 and $R_{13}$ is $C_{1-6}$alkyl or hydrogen, with the proviso that when n is 0, $R_5$ is hydrogen and further that $R_7$, $R_8$ and $R_9$ are not all hydrogen;
$R_{14}$ and $R_{15}$ are independently hydrogen or $C_{1-4}$alkyl at any point when d is not 0;
d is 0 to 6;

W is a six membered aryl or heteroaryl ring selected from phenyl, pyridyl or pyrimidyl, unsubstituted or substituted with G, E, or D; or a five membered heteroaryl ring selected from tetrazolyl, thiazolyl, triazolyl, thienyl, furyl, oxazolyl, thiadiazolyl, pyrolyl, imidazolyl or pyrazolyl, unsubstituted or substituted with G; or W is one of

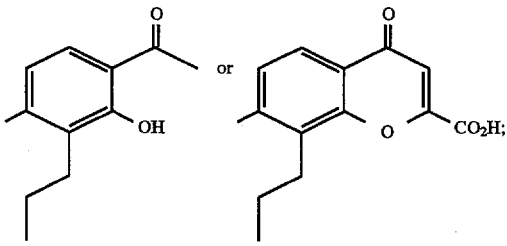

G is

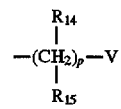

wherein $R_{14}$ and $R_{15}$ are independently hydrogen or $C_{1-4}$alkyl;
p is 0 to 6;
V is H, $C_{1-4}$alkyl, COR', $SO_3H$, $SO_2H$, $SO_2NH_2$, $COCH_2OH$, $CHOHCH_2OH$, or tetrazolyl, with R' as defined above; and E and D are independently selected from H, OH, F, Cl, Br, $CF_3$, $C_{1-4}$alkyl, $C_{1-4}$alkoxy, methylthio, trifluoromethylthio, $NO_2$, $NH_2$, $NHC_{1-4}$alkyl, or $C_{1-4}$alkylCO;

and pharmaceutically acceptable salts thereof, are leukotriene antagonists and are useful for treating allergic and inflammatory disease states. Such compounds, and methods for preparing the compounds, are disclosed in U.S. Pat. No. 4,820,719, U.S. Pat. No. 4,874,792, EP-A 0 365 149, EP-A 0 358 240, EP-A 0 313 697, EP-A 0 296 732 and EP-A 0 291 731, the disclosures of which are incorporated herein by reference.

A common step in the synthesis of the compounds of formula (I) focuses upon the reaction of a substituted epoxy ester of formula (II):

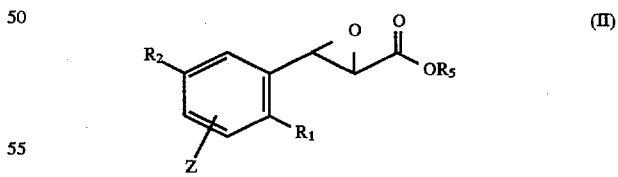

wherein $R_1$, $R_2$ and A are as defined for formula (I), and $R_5$ is lower alkyl, with a mercaptan of formula (III):

wherein $R_3$ is defined according to formula (I), with any functional groups optionally protected, to introduce the 2-hydroxy-3-sulfido moieties. This reaction is described in the above cited references and is represented in Scheme (A).

3

Scheme A

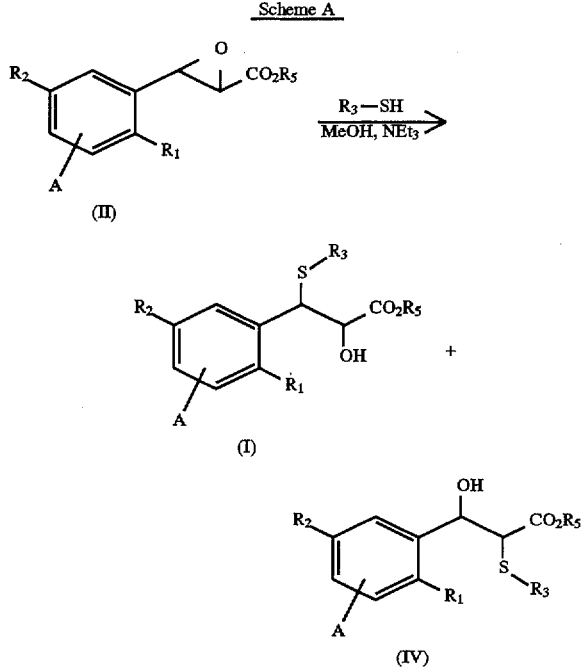

One problem encountered in this method of preparation is a lack of regiocontrol, such that the Sulfido moiety is introduced in both the 2- and 3-positions to produce the desired 2-hydroxy-3-sulfido compound (I) and an undesired 2-sulfido-3-hydroxy compound (IV). Accordingly, Gleason et al., *J. Med. Chem.*, 30, 959 (1987), report a 1:1 mixture of regioisomers (I) and (IV) in the preparation of [R-(R*, S*)]-β-[(2-carboxyethyl)thio)]-α-hydroxy-2-(8-phenyloctyl)benzenepropanoic acid, by this method. Lack of regiocontrol results in low yields of the desired 2-hydroxy-3-sulfido isomer and greatly increases manufacturing costs. A method for producing a regioselective opening of the epoxy intermediates given by formula (II) is therefore desirable. Suitable methods for selectively producing the compounds of formula (I) from the G-epoxy esters of formula (II) have not been disclosed.

Chong, et al., *J. Org. Chem.*, 50, 1560 (1985), disclose methods for controlling the regioselectivity of epoxide openings for certain α-epoxy acids and α-epoxy amides. Accordingly, Chong et al. report that, in the presence of titanium tetraisopropoxide, aliphatic α-epoxy acids and secondary amides, when reacted with thiophenol, diethylamine, cyanide or azide ions, show a preference for opening the epoxide in the β-position. Titanium reagents are generally undesirable for large scale industrial applications due to waste disposal and environmental problems.

In the absence of titanium tetraisopropoxide, most α,β-epoxy acids are attacked preferentially at the α-position by nucleophiles, such as amines and thiolates. See Chong et al., *J. Org. Chem.*, 50, 1560. (1985); Sharpless et al., *Pure Appli. Chem.*, 55, 589 (1983); Liwschitz et al., *J. Chem. Soc.*, 1116 (1962); Harada et al., *Bull. Chem. Soc. Jpn.*, 39, 2311 (1966). However, Harada, *J. Org. Chem.*, 31, 1407 (1966) reports that ammonia adds with modest selectivity (about 3:1) to the β-carbon of the potassium salt of trans-phenylglycidic acid. Harada et al., *Bull. Chem. Soc. Jpn.*, 47, 2911 (1974), report that the same reaction proceeds with high β-selectivity (about 30:1) on the ephedrine salt of cis-phenylglycidic acid.

Mohrig et al., *J. Org. Chem.*, 46, 4655 (1981), report that the sodium salt of α,β-epoxybutanoic acid is preferentially

4 reduced by sodium:borohydride in the α-position, and that the preference is altered to favor reduction in the β-position when lithium bromide is added to the reaction mixture.

There is, therefore, a need for new intermediates and processes which can induce thiols to react in a regioselective manner with 2,3-epoxy-3-phenylpropanoic acids.

SUMMARY OF THE INVENTION

It is an object of this invention to provide a new and efficient process for the preparation of compounds of formula (V). Accordingly, this invention is a process for preparing compounds of formula (V):

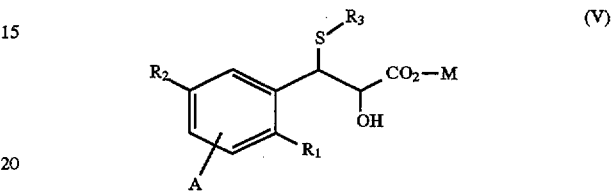

wherein:
$R_1$ is $(L)_a$—$(CH_2)_b$—$(T)_c$—B;
a is 0 or 1;
b is 3 to 14;
c is 0 or 1;
L and T are independently sulfur, oxygen, CH=CH, C≡C, or $CH_2$;
B is H, $C_{1-4}$alkyl, ethynyl, trifluoromethyl, isopropenyl, furanyl, thienyl, cyclohexyl or phenyl optionally monosubstituted with Br, Cl, $CF_3$, $C_{1-4}$alkoxy, $C_{1-4}$alkyl, methylthio or trifluoromethylthio;
M is H, Li, Na, K, $NH_4$ or an organic ammonium cation;
$R_2$ and A are independently Selected from H, $CF_3$, $C_{1-4}$alkyl, $C_{1-4}$alkoxy, F, Cl, Br, I, OH, $NO_2$ or $NH_2$; or, when $R_1$ and A are H, $R_2$ is $(L)_a$—$(CH_2)_b$—$(T)_c$—B wherein a, b, c, L, T and B are as defined above;
$R_3$ is $(CH_2)_n CH(R_5)COR_6$, $CH(CO_2H)CH_2CO_2H$, $CH_2CH_2Z$,

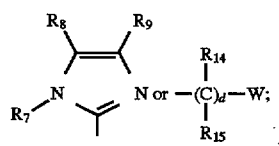

n is 0 to 6;
$R_5$ is hydrogen, amino, or $NHCOCH_2CH_2CH(NH_2)CO_2H$;
$R_6$ is hydroxy, amino, $NHCH_2CO_2H$ or $C_{1-6}$alkoxy;
Z is $SO_3H$, $SO_2NH_2$ or CN;
$R_7$ is hydrogen, $C_{1-4}$alkyl or $C_{3-4}$alkenyl;
$R_8$ is hydrogen, $C_{1-4}$alkyl, carboxyl, carboxamido, or $(CH_2)_p CO_2R_{12}$, wherein p is 1 or 2 and $R_{12}$ is $C_{1-6}$alkyl or hydrogen when $R_7$ and $R_9$ are hydrogen or $C_{1-4}$alkyl;
$R_9$ is hydrogen, $C_{1-4}$alkyl, or $(CH_2)_p CO_2R_{13}$, wherein p is 1 or 2 and $R_{13}$ is $C_{1-6}$alkyl or hydrogen, with the proviso that when n is 0, $R_5$ is hydrogen and further that $R_7$, $R_8$ and $R_9$ are not all hydrogen;
$R_{14}$ and $R_{15}$ are independently hydrogen or $C_{1-4}$alkyl at any point when d is not 0;
d is 0 to 6;
W is a six membered aryl or heteroaryl ring selected from phenyl, pyridyl or pyrimidyl, unsubstituted or substituted with G, E, or D; or a five membered heteroaryl ring selected from tetrazolyl, thiazolyl, triazolyl, thienyl, furyl, oxazolyl, thiadiazolyl, pyrolyl, imidazolyl or pyrazolyl, unsubstituted or substituted with G; or W is one of

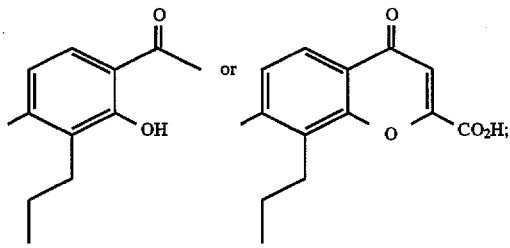

G is

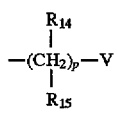

wherein $R_{14}$ and $R_{15}$ are independently hydrogen or $C_{1-4}$alkyl;

p is 0 to 6;

V is H, $C_{1-4}$alkyl, COR', $SO_3H$, $SO_2H$, $SO_2NH_2$, $COCH_2OH$, $CHOHCH_2OH$, or tetrazolyl;

R' is OH, $NH_2$, aryloxy or $C_{1-6}$alkoxy; and

E and D are independently selected from H, OH, F, Cl, Br, $CF_3$, $C_{1-4}$alkyl, $C_{1-4}$alkoxy, methylthio, trifluoromethylthio, $NO_2$, $NH_2$, $NHC_{1-4}$alkyl, or $C_{1-4}$alkylCO, with any functional groups optionally protected;

by reacting a compound of formula (VI):

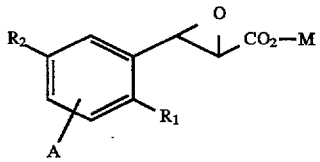

wherein $R_1$, $R_2$, A and M are as defined above for formula (V), with a compound of the formula $R_3$—SH, wherein $R_3$ is as defined above for formula (V), with any reactive groups optionally protected, and a base.

A feature of this invention is a novel intermediate compound according to formula (VI):

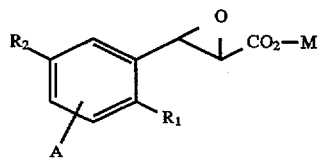

wherein $R_1$, $R_2$, A, and M are as defined above for formula (V).

DETAILED DESCRIPTION OF THE INVENTION

The present invention discloses novel intermediates according to formula (VI):

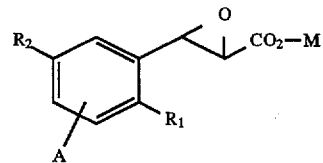

wherein $R_1$ is $(L)_a$—$(CH_2)_b$—$(T)_c$—B;

a is 0 or 1;

b is 3 to 14;

c is 0 or 1;

L and T are independently sulfur, oxygen, CH=CH, C≡C, or $CH_2$;

B is H, $C_{1-4}$alkyl, ethynyl, trifluoromethyl, isopropenyl, furanyl, thienyl, cyclohexyl or phenyl unsubstituted or monosubstituted by Br, Cl, $CF_3$, $C_{1-4}$alkoxy, $C_{1-4}$alkyl, methylthio or trifluoromethylthio;

$R_2$ and A are independently selected from H, $CF_3$, $C_{1-4}$alkyl, $C_{1-4}$alkoxy, F, Cl, Br, I, OH, $NO_2$ or $NH_2$; or, when $R_1$ and A are H, $R_2$ is $(L)_a$—$(CH_2)_b$—$(T)_c$—B wherein a, b, c, L, T and B are as defined above; and M is H, Li, Na, K, NH4 or an organic ammonium cation.

Suitably $R_1$ is —$(CH_2)_b$—phenyl or —$(CH_2)_b$—$CH_3$.

Preferably $R_1$ is phenyloctyl.

Suitably $R_2$ and A are H.

Preferably M is H or Li.

Preferred compounds are:

trans-3-[2-(8-phenyloctyl)phenyl]oxiranecarboxylic acid;

Trans-3-[2-(8-phenyloctyl)phenyl]oxiranecarboxylic acid lithium salt;

2R-trans-3-[2-(8-phenyloctyl)phenyl]oxiranecarboxylic acid; and 2R-trans-3-[2-(8-phenyloctyl)phenyl]oxiranecarboxylic acid lithium salt.

An especially preferred compound is trans-3-[2-(8-Phenyloctyl)phenyl]oxiranecarboxylic acid.

$C_{1-4}$alkyl means an alkyl group containing one to four carbon atoms. Examples of $C_{1-4}$alkyl are methyl, ethyl, propyl, isopropyl, butyl, isobutyl, sec-butyl and tert-butyl. $C_{1-6}$alkyl similarly means an alkyl group containing one to six carbon atoms. Aryloxy as used herein for R' means phenyl optionally substituted with one or two $C_{1-4}$alkyl, $C_{1-4}$alkoxy, F, Cl, Br, I, OH, $CF_3$, $NO_2$ or $NH_2$. An organic ammonium cation is a compound which contains a nitrogen atom bound to one or more organic radicals and bears a formal positive charge. Typical organic radicals are $C_{1-5}$alkyl, aryl or heteroaryl. Examples of organic ammonium cations are diethylammonium, triethylammonium, anilinium, pyridinium or piperidinium.

The novel intermediates of formula (VI), wherein M is Li, K or Na, are prepared by reacting a compound of formula (VII):

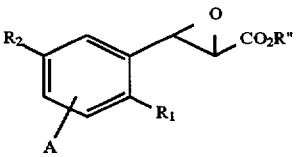

wherein $R_1$, $R_2$ and A are as defined for formula (VI) and R" is $C_{1-5}$alkyl or aryl, with water and a strong base. In particular, aryl esters are intended to include, but not be limited to, phenyl or naphthyl unsubstituted or substituted by one or two halogen, $C_{1-4}$alkyl, $C_{1-4}$alkoxy or trifluoromethyl groups. Common methods for preparing compounds of formula (VII) are described in U.S. Pat. No. 4,820,719, U.S. Pat. No. 4,874,792 and copending application U.S. Ser. No. 07/366,059, which are incorporated herein by reference.

Suitable reagents for converting the compounds of formula (VII) to the compounds of formula (VI) are alkali metal hydroxides or carbonates, although any base which effectively hydrolyzes an ester function without modifying the epoxide moiety is suitable. It will be understood that any preparation of the glycidic acid or a salt of the acid is suitable, since common methods of the chemical art, such as the use of ion exchange resins, may be used to interconvert salts and acids.

Typically, an alkali metal hydroxide, such as lithium, sodium or potassium hydroxide, is dissolved in an amount of water and combined with a solution of the compound of formula (VII). Generally the epoxy-ester is dissolved in an organic co-solvent to facilitate the reaction. Although any organic solvent in which the epoxy-ester is soluble is acceptable, water miscible solvents, such as acetone, lower alkyl alcohols or tetrahydrofuran, are especially suitable. Less water soluble co-solvents are also acceptable, but the reaction conditions may require routine modification, such as the addition of a suitable phase transfer reagent, to effect the desired hydrolysis. The salt resulting from the hydrolysis reaction may be precipitated or crystallized from the reaction mixture directly, and optionally recrystallized.

The carboxylic acids of formula (VI), wherein M is H, are prepared by basic hydrolysis of the intermediates of formula (VII), acidification, extractive workup and crystallization of the free acid. The carboxylic acid may then be converted to other desired salts of formula (VI) by routine procedures, such as treatment with an appropriate salt forming reagent followed by precipitation or crystallization. Alternatively, the salt may be prepared and used in situ. Typical salt forming reagents are alkali metal hydroxides, alkoxides, alkyls, hydrides or amides, or ammonium hydroxide or amines. The acids of formula (VI) may also be prepared by treatment of any salt of the epoxy acid with an acid, such as hydrochloric acid The compounds of formula (VI) are used in a process for the preparation of compounds of formula (V):

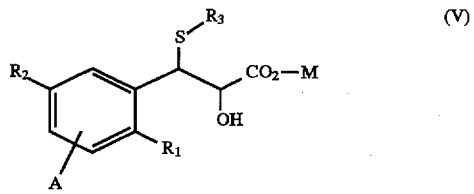

wherein:

$R_1$ is $(L)_a$—$(CH_2)_b$—$(T)_c$—B;

a is 0 or 1;

b is 3 to 14;

c is 0 or 1;

L and T are independently sulfur, oxygen, CH=CH, C≡C, or $CH_2$;

B is H, $C_{1-4}$alkyl, ethynyl, trifluoromethyl, isopropenyl, furanyl, thienyl, cyclohexyl or phenyl unsubstituted or monosubstituted by Br, Cl, $CF_3$, $C_{1-4}$alkoxy, $C_{1-4}$alkyl, methylthio or trifluoromethylthio;

M is H, Li, Na, K, $NH_4$ or an organic ammonium cation;

$R_2$ and A are independently selected from H, $CF_3$, $C_{1-4}$alkyl, $C_{1-4}$alkoxy, F, Cl, Br, I, OH, $NO_2$ or $NH_2$ or, when $R_1$ and A are H, $R_2$ is $(L)_a$—$(CH_2)_b$—$(T)_c$—B wherein a, b, c, L, T and B are as defined above;

$R_3$ is $(CH_2)_n CH(R_5)COR_6$, $CH(CO_2H)CH_2CO_2H$, $CH_2CH_2Z$,

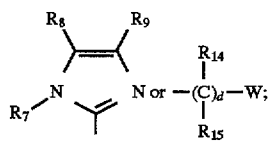

n is 0 to 6;

$R_5$ is hydrogen, amino, or $NHCOCH_2CH_2CH(NH_2)CO_2H$;

$R_6$ is hydroxy, amino, $NHCH_2CO_2H$ or $C_{1-6}$alkoxy;

Z is $SO_3H$, $SO_2NH_2$ or CN;

$R_7$ is hydrogen, $C_{1-4}$alkyl or $C_{3-4}$alkenyl;

$R_8$ is hydrogen, $C_{1-4}$alkyl, carboxyl, carboxamido, or $(CH_2)_p CO_2 R_{12}$, wherein p is 1 or 2 and $R_{12}$ is $C_{1-6}$alkyl or hydrogen when $R_7$ and $R_9$ are hydrogen or $C_{1-4}$alkyl;

$R_9$ is hydrogen, $C_{1-4}$alkyl, or $(CH_2)_p CO_2 R_{13}$, wherein p is 1 or 2 and $R_{13}$ is $C_{1-6}$alkyl or hydrogen, with the proviso that when n is 0, $R_5$ is hydrogen and further that $R_7$, $R_8$ and $R_9$ are not all hydrogen;

$R_{14}$ and $R_{15}$ are independently hydrogen or $C_{1-4}$alkyl at any point when d is not 0;

d is 0 to 6;

W is a six membered aryl or heteroaryl ring selected from phenyl, pyridyl or pyrimidyl, unsubstituted or substituted with G, E, or D; or a five membered heteroaryl ring selected from tetrazolyl, thiazolyl, triazolyl, thienyl, furyl, oxazolyl, thiadiazolyl, pyrolyl, imidazolyl or pyrazolyl, unsubstituted or substituted with G; or W is one of

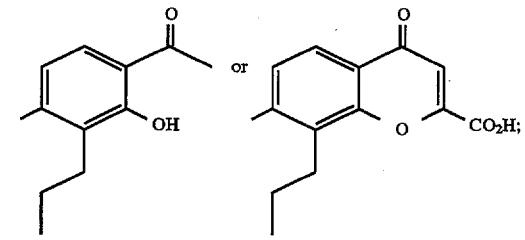

G is

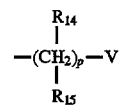

wherein $R_{14}$ and $R_{15}$ are independently hydrogen or $C_{1-4}$alkyl;

p is 0 to 6;

V is H, $C_{1-4}$alkyl, COR', $SO_3H$, $SO_2H$, $SO_2NH_2$, $COCH_2OH$, $CHOHCH_2OH$, or tetrazolyl;

R' is OH, $NH_2$, aryloxy or $C_{1-6}$alkoxy; and

E and D are independently selected from H, OH, F, Cl, Br, $CF_3$, $C_{1-4}$alkyl, $C_{1-4}$alkoxy, methylthio, trifluoromethylthio, $NO_2$, $NH_2$, $NHC_{1-4}$alkyl, or $C_{1-4}$alkylCO; and pharmaceutically acceptable salts thereof;

which process comprises reacting a compound of formula (VI):

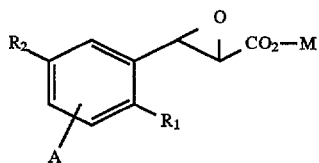

wherein $R_1$, $R_2$, A and M are as defined above for formula (V), with a compound of the formula:

$R_3S-H$ wherein $R_3$ is as defined above for formula (V), with any reactive groups optionally protected, and a base.

Suitably $R_3$ is $CH_2CH_2COR_6$, or phenyl substituted with COR', or 4-methoxybenzyl Suitably M is H or Li.

Suitably A and $R_2$ are H.

Generally, the reaction is carried out by combining a compound of formula (VI) and the mercaptan, $R_3$—SH, with a base in a suitable organic solvent. Although not critical, the reaction is typically carried out between −15° C. and 25° C. or room temperature. An especially suitable temperature range is −10° C. to 10° C.

The reaction proceeds as a nucleophilic opening of the epoxide to yield inversion of configuration at the 3-position of the compounds of formula (VI). Thus, when the compound of formula (VI) is nonracemic, the 2-hydroxy-3-sulfido-3-phenylpropanoic acid product is also nonracemic.

Reactive groups which may be optionally protected include carboxylic or sulfonic acid, hydroxyl and imidazole functionalities. Common methods for protection and deprotection of these moieties is described in Greene, "Protective Groups in Organic Synthesis", John Wiley and Sons, New York (1981). Acids are normally protected by forming aryl, aralkyl or aliphatic esters, such as $C_{1-6}$alkyl, phenyl, naphthyl or benzyl esters, and are deprotected by normal methods of hydrolysis or hydrogenation. The hydroxyl group is commonly protected as an ether, particularly a silyl ether, or an ester. Tetrahydropyranyl-, trimethylsilyl and t-butyldimethylsilyl-ethers, and acetyl- and benzoyl-esters are representative protecting groups for the hydroxyl moiety. The imidazole group is commonly protected by a t-butyloxycarbonyl (Boc) or trimethylsilylethoxymethyl (SEM) group. These protecting groups are commonly removed by acid treatment.

Examples of suitable organic solvents are ether-type or halocarbon solvents such as tetrahydrofuran, diethyl ether, dimethoxyethane, methylene chloride or chloroform, or mixtures thereof. Tetrahydrofuran is preferred.

Although an excess of mercaptan is not critical, use of 1 to 2 equivalents is typical. Bases which are sufficiently strong to partially ionize the mercaptan are acceptable. Examples of suitable bases are alkali metal alkyls, alkoxides, hydroxides, hydrides and amides, basic ammonium compounds and amines. Typical bases are lithium, sodium or potassium hydride, hydroxide or alkoxide, butyl lithium, lithium diisopropylamide or triethylamine. An alkali metal hydroxide or alkoxide is especially suitable.

The amount of base used to promote the reaction is not critical. If the starting epoxide is a salt, 0.01 to 1.0 equivalents of base, relative to mercaptan, is suitable. If the starting epoxide is a carboxylic acid, then an additional amount of base, equal to one equivalent of the epoxide, may be used. In such case, an alkali metal base is used to convert the acid to the salt in situ. It is also possible to convert the mercaptan to a mercaptide using base, which in turn may be used to convert the carboxylic acid to its salt in situ.

The order of addition is also not critical. The base may be added to a mixture of the mercaptan and epoxide, the epoxide may be added to the mercaptan and base, or the mercaptan may be added to the mixture of the epoxide and base.

The 2-hydroxy-3-sulfido product of this reaction is isolated and purified by routine methods in the chemical art. Usually extractive workup is accomplished by optionally concentrating the reaction mixture, adding water, acidifying the reaction mixture and extracting with a suitable solvent. Ethyl acetate, diethyl ether, toluene, tetrahydrofuran, chloroform and methylene chloride are suitable extraction solvents. Upon removal of the extraction solvent, the product may be crystallized.

Using the procedure of this invention the resulting product (V) contains greater than 65% of the desired 2-hydroxy-3-sulfido-3-aryl-propionate regioisomer, and generally greater than 95% of this desired regioisomer. The product of this reaction may be transformed to other intermediate products which may be useful in producing the compounds of this invention by well known methods.

EXAMPLES

The nomenclature and abbreviations common to the chemical art are used in the examples. Unless otherwise noted, reagents were obtained from commercial suppliers and were used without further purification. Solvents were obtained from commercial suppliers as Reagent grade and were used without further purification. Melting points were taken on a Thomas-Hoover capillary melting point apparatus and are uncorrected. IR spectra were recorded on a Perkin-Elmer Model 283 infrared spectrophotometer. FT-IR spectra were obtained on a Nicolet 6000 FT infrared spectrometer. Combustion analyses were run on a Perkin-Elmer 240 C elemental analyzer. NMR spectra were obtained with a Bruker Instruments WM 400 or WM 360,or with a Jeol 270 spectrometer. Chemical shifts are reported in ppm (δ) downfield from tetramethylsilane. Annotations to $^1$H-NMR are as follows: s, singlet; d, doublet; t, triplet; br, broad; m, multiplet; J, coupling constant in Hertz.

Example 1

Preparation of trans-3-[2-(8-phenyloctyl)phenyl]oxiranecarboxyl acid

To a solution of 2-(8-phenyloctyl)benzaldehyde (207.26 g, 0.68 mol), 2-propanol (300 mL) and methyl chloroacetate (90.2 mL, 1.02 mol) was added sodium methoxide (25% in methanol, 220.2 g, 1.02 mol). The mixture was stirred at 40° C. until the reaction was complete by HPLC then cooled to 0° C. A solution of sodium hydroxide (2510 g, 0.63 mol) in deionized water was added and the mixture stirred until hydrolysis was complete. The product was partitioned between ethyl acetate and deionized water, then acidified with 6N hydrochloric acid. The layers were separated. The organic layer was washed with aqueous sodium chloride, then concentrated in vacuo to a viscous oil. The product was precipitated from a mixture of ethyl acetate and hexanes, isolated by filtration, washed with hexanes, then dried in vacuo to afford crystalline needles (164.2 g) : mp 75.5°–76° C.; $^1$H NMR (DMSO-$d_6$, 400 MHz) δ 13.32 (s, 1H), 7.28–7.03 (m, 9H), 4.21 (s, 1H), 3.42 (s, 1H), 2.80–2.72 (m, 1H), 2.65–2.51 (m, 3H), 1.52 (m, 4H), 1.26 (s, 8H).

Example 2

Preparation of trans-3-[2-(8-phenyloctyl)phenyl]-oxiranecarboxylic acid lithium salt To a solution of the compound of Example 1 (101.0 g, 0.28 mol) in 2-propanol (1000 mL) was added a solution of lithium hydroxide monohydrate (12.9 g, 0.30 mol) in deionized water (56 mL). After cooling the slurry, the product was isolated by filtration, washed with 2-propanol, then dried in vacuo to afford a white solid (255.8 g) : mp 153°–157° C.; IR (KBr) 3600–3100, 3100–3000, 3000–2800, 165.4, 1610, 1430, 1281, 892, 757, 748, 698 cm$^{-1}$; $^1$H NMR (DMSO-d$_6$, 27.0 MHz) δ 7.28–7.05 (m, 9H), 3.92 (d, 1H, J=1.95 Hz), 2.97 (d, 1H, J=2.44 Hz), 2.69–2.51 (m, 4H), 1.53 (m, 4H), 1.26 (s, 8H); $^{13}$C NMR (DMSO-d$_6$, 67.5 MHz) δ 170.05, 142.27, 140.45, 135.59, 128.79, 128.19, 128.13, 127.21, 125.86, 125.48, 123.92, 60.00, 53.64, 35.15, 31.96, 31.01, 30.49, 28.88, 28.64.

Example 3

Preparation of 2R-trans-(2-naphthalenyl) 3-[2-(8-phenyloctyl)phenyl]oxiranecarboxylate a) Preparation of (E)-1-(2-naphthalenyl)-3-[2-(8-phenyloctyl)phenyl]-2-propen-1-one.

To a cooled (5° C.) solution of ethanol (95%, 3.53 L) in a 12 L 3-neck flask, under nitrogen, was added sodium metal (36.8 g, 1.16 mol) over a period of 30 min. After the sodium had dissolved, stirring was continued for 5 min, and 2-(8-phenyloctyl)-benzaldehyde (200 g, 0.68 mol) was added. The reaction was cooled to 10° C. and 2-acetonaphthone (115.6 g, 0.679 mol) was added in one portion. The reaction was seeded with the desired product (2 g) and stirred for 18 h at ambient temperature. A yellow precipitate was present after that time. The reaction was treated with ice water (350 mL), cooled to 10° C., and filtered. The filter cake was washed with 50% aqueous ethanol (400 mL). The product, a yellow solid, was air dried and any lumps were pulverized. The product was dried at 25° C. (0.1 mm Hg) for 24 h (248 g, 89%): mp 41.0°–42.5° C.; IR (KBr) 1658, 1597, 1467, 1325, 1185, 1124, 1016, 970, 763 cm$^{-1}$; $^1$H NMR (CDCl$_3$, 360 MHz) δ 8.55 (d, 1 H, naphthyl-1H, J=1.2 Hz), 8.21 (d, 1 H, J=15.5 Hz, olefinic proton), 7.12–8.11 (m, 15 H), 7.62 (d, 1 H, J=15.6 Hz), 2.75 (t, 2 H, J=7.71 Hz), 2.57 (t, 2 H, J=7.71 Hz), 1.59 (b, 4 H), 1.29 (b, 8 H); $^{13}$C NMR (CDCl$_3$) δ 190.25, 143.31, 142.86, 142.40, 135.59, 135.46, 133.47, 132.57, 130.21, 130.15, 129.91, 129.47, 128.52, 128.34, 128.15, 127.79, 126.72, 126.58, 126.31, 125.47, 124.49, 123.34, 35.91, 33.39, 31.72, 31.42, 29.41, 29.38, 29.34, 29.23; TLC R$_f$ 0.55 (CH$_2$Cl$_2$: n-hexane, 3:1, Silica gel GF); HPLC RT 17.7 min (Waters μ-Bondapak® C-18; 30×3.9 mm; CH$_3$CN:water, 85:15; 1.5 ml/min; UV detection at 230 nm). Anal. Calcd for C$_{33}$H$_{34}$O: C, 88.74; H, 7.67. Found: C, 88.84; H, 7.68.

b) Preparation of 2R-trans-(2-naphthalenyl)-[3-[2-(8phenyloctyl)phenyl]oxiranyl]methanone.

To sodium hydroxide (255 g, 6.37 mol) dissolved in water (650 mL) at 14°–18° C. was added poly-L-leucine (215 g) followed by a mixture of the compound of Example 3a (250 g, 0.531 mol) and n-hexane (4.0 L). The heterogeneous mixture was stirred at ambient temperature for 16 h, then cooled to 10°–15° C. in an ice bath. Ethylenediaminetetraacetic acid disodium salt dihydrate (5 g) was added followed by hydrogen peroxide (H$_2$O$_2$ 30% in water, 1.126 L, 10.93 mol) at such a rate that the reaction temperature did not exceed 25° C. The flow of the hydrogen peroxide was directed below the surface of the reaction by a polypropylene tube attached to the dropping funnel. This addition required 2–3 h. The reaction was stirred at 20°–24° C. for 20 h. The reaction was treated with ethyl acetate (300 mL), and the reaction mixture filtered through a jacketed bench Buchner funnel (40°–50° C.). The precipitate (consisting of poly-L-leucine and some product) was washed with boiling ethyl acetate, then slurried in ethyl acetate (1.5 L) at 40°–50° C. for 10–20 min and refiltered. The combined filtrates were placed in a separatory funnel and washed with water (3×500 mL) and brine (1 L). The organic layer was dried (MgSO$_4$, 300 g), filtered, and evaporated (30°–40° C., 14 mm Hg) to yield a white solid. The product was dissolved in boiling n-hexane-toluene (95:5, 1.90 L), and the hot solution was filtered to remove any insolubles. The solution was kept at ambient temperature for 1.5 h, then placed in a refrigerator at 5° C. for 12 h. The crystalline product was filtered and washed with a small portion of the filtrate and cold hexane (100 mL). The product was air dried for 3 h and then placed in a vacuum desiccator (1 mm Hg, 25° C.) for 24 h, yielding the titled product (200 g, 82%), which assayed at 96–97% e.e. by HPLC; mp 62°–63° C.; [ζ]$_D$+26.6° (c 1.0, CH$_2$Cl$_2$), [α]$_{546}$+31.1°; IR (nujol) 1672, 1403, 1280, 1223, 750 (br), 692 cm$^{-1}$; $^1$H NMR (CDCl$_3$, 360 MHz) δ 8.59 (d, 1 H, J=1.30 Hz), 7.12–8.10 (m, 15 H), 4.36 (d, 1 H, J=1.94 Hz), 4.33 (d, 1 H, J=1.94 Hz), 2.66 (m, 2 H), 2.50 (t, 2 H, J=7.75 Hz), 1.42–1.60 (m, 4 H), 1.02–1.19 (m, 8 H); $^{13}$C NMR (CDCl$_3$) δ 193.13, 142.89, 141.47, 136.02, 133.56, 133.00, 132.49, 130.47, 129.72, 129.37, 129.06, 128.93, 128.55, 128.39, 128.22, 127.91, 127.12, 126.47, 125.56, 124.31, 123.69, 60.48, 57.67, 35.85, 32.73, 31.18, 29.39, 29.18, 29.10; TLC R$_f$ 0.35 (CHCl$_3$, Silica gel GF), 0.43 (CH$_2$Cl$_2$:n-hexane, 3:1); HPLC RT 12.1 min (2R-enantiomer), 18.8 min (2S-enantiomer) (OP (+); 25 cm×4.6 mm; CH$_3$OH; 0.8 mL/min; UV detection at 23.1 nm), RT 6.0 min (Waters μ-Bondapak® C-18; 30 cm×3.9 mm; CH$_3$CN:water, 9:1; 2 mL/min; UV detection at 211 nm). Anal. Calcd for C$_{33}$H$_{34}$O$_2$: C, 85.67; H, 7.40. Found C, 85.93; H, 7.48.

c) Preparation of 2R-trans-(2-naphthalenyl)-3-[2-(8phenyloctyl)-phenyl]oxiranecarboxylate.

To a solution of 3-chloroperbenzoic acid (85%; 28 g, 0.162 mol) in methylene chloride (300 mL) was added 2R-trans-(2-naphthalenyl)-[3-[2-(8-phenyloctyl)phenyl] oxiranyl]methanone (29 g, 0.062 mol) from Example 3b. The solution was stirred at reflux for 4 h, cooled to 15° C., and the precipitated 3-chlorobenzoic acid was removed by filtration. The solvent was evaporated at <35° C., and the thick residue dissolved in hot isopropanol:toluene (9:1, 300 ml), and allowed to reach room temperature. The mixture was cooled in the refrigerator for 20 h, and the product filtered and dried (25° C, 0.1 mm Hg) to give the desired ester (25 g, 81%, >99.8% e.e. by HPLC). Mp 82°–83° C.; [α]$_D$ –89.5 (c 1, CH$_2$Cl$_2$), [α]$_{546}$ –109.9; IR (nujol) 1752 (s), 1370, 1247, 1210, 1177 (br), 890, 740, 750 cm$^{-1}$; (KBr) 2920, 2850, 1762 (s), 1469, 1337, 1216, 1183, 900, 809, 746, 699 cm$^{-1}$; $^1$H NMR (CDCl$_3$, 360 MHz) δ 7.14–7.91 (m, 16 H), 4.49 (d, 1 H, J=1.51 Hz, oxirane proton), 3.70 (d, 1 H, J=1.72 Hz, oxirane proton), 2.80 (m, 2 H), 2.56 (t, 2 H, J=7.72 Hz), 1.64 (m, 4 H), 1.34 (br, 8 H); $^{13}$C NMR (CDCl$_3$) δ 167.05, 147.88, 142.81, 141.43, 133.70, 132.61, 131.68, 129.65, 129.38, 128.69, 128.34, 128.18, 127.82, 127.71, 126.80, 126.40, 126.01, 125.53, 124.45, 120.43, 118.30, 56.60, 56.22, 35.90, 32.89, 31.38, 31.19, 29.61, 29.45, 29.28; TLC R$_f$ 0.55 (CHCl$_3$, Silica gel GF); HPLC RT 7.25 min (Waters μ-Bondapak® C-18; 30 cm×3.9 mm; CH$_3$CN:water, 9:1; 2 mL/min; UV detection at 220 nm); RT 25.7 min, (2R-enantiomer); 30.46 min (2S-enantiomer); (Baker Chiralpak® OP(+); 25 cm×4.5 mm; CH$_3$OH; 0.50 mL/min; UV detection at 220 nm). Anal. Calcd for C$_{33}$H$_{34}$O$_3$: C, 82.80; H, 7.20. Found: C, 82.92; H, 7.09.

Example 4

Preparation of 2R-trans-3-[2-(8-phenyloctyl)phenyl] oxiranecarboxylic acid lithium salt To a mixture of 2R-trans-(2-naphthalenyl)3-[2-(8phenyloctyl)phenyl]oxiranecarboxylate (1.0 kg, 2.09 mol)

in absolute methanol (6 L) was added a solution of lithium hydroxide monohydrate (268.4 g, 6.27 mol) in deionized water (1.75 L) at room temperature over a 20 min period, allowing the temperature to rise to 34° C. After the disappearance of the naphthyl ester (15–30 min) 9000 mL of hot (75° C.) deionized water was added to the mixture. The mixture was further warmed to 65° C. to obtain a clear homogeneous solution. The product was allowed to crystallize as the solution was slowly cooled to ~5° C. The product was filtered, washed and dried in vacuo to afford a white crystalline solid (702.0 g, 95.4%): mp 176.0°–178.5° C.; $[\alpha]_D$ –33.9° (c 1.0, $CH_3OH$); FT-IR (KBr) 3600–3100, 3100–3000, 3000–2800, 1615, 1446, 1312, 765, 752, 735, 965 $cm^{-1}$; $^1H$ NMR (DMSO-$d_6$, 400 MHz) δ 7.28–7.04 (m, 9H), 3.86 (d, 1H, J=2.1 Hz), 2.88 (d, 1H, J=2.0 Hz), 2.71–2.50 (m, 4H), 1.54–1.52 (m, 4H), 1.26 (s, 8H); $^{13}C$ NMR (DMSO-$d_6$, 100 MHz) δ 169.98, 142.32, 140.50, 135.65, 128.87, 128.25, 128.19, 127.27, 125.93, 125.55, 123.97, 60.12, 53.64, 35.17, 31.98, 31.04, 30.52, 28.91, 28.68. Anal. Calcd for $C_{23}H_{27}O_3Li$: C, 77.08; H, 7.59. Found: C, 77.25; H, 7.85.

Example 5

Preparation of (R*, S*)-(±)-β-[(2-carboxyethyl)thio]-α-hydroxy-2-(8-phenyloctyl)benzenepropanoic acid To a cooled (0° C.) solution of the compound of Example 2 (90.5 g, 0.25 mol), tetrahydrofuran (685 mL) and methyl 3-mercapto-propionate (37.3 g, 0.31 mol) was added sodium methoxide (25% in methanol, 2.68 g, 12.4 mmol). The mixture was stirred at 0° C. until the reaction was complete by HPLC. 2.5N Sodium hydroxide (222.5 mL, 0.56 mol) was added and the mixture stirred until hydrolysis was complete. The solution was acidified with hydrochloric acid and the layers were separated. The organic phase was washed with aqueous sodium chloride and concentrated in vacuo to a viscous oil. The product was precipitated from a mixture of ethyl acetate and hexanes. After cooling the slurry, the product was isolated by filtration, washed with hexanes, and dried in vacuo to afford a white powder (113.59 g): $^1H$ NMR (DMSO-$d_6$, 400 MHz) δ 12.42 (s, 2H), 7.50 (s, 1H), 7.28–7.11 (m, 8H), 5.74 (s, 1H), 4.35 (s, 2H), 2.71–2.50 (m, 6H), 2.40–2.31 (m, 2H), 1.56 (m, 4H), 1.30 (s, 8H) $^{13}C$ NMR (DMSO-$d_6$, 90 MHz) δ 173.56, 172.73, 142.32, 140.68, 136.76, 128.93, 128.62, 128.24, 128.18, 126.74, 125.54, 73.01, 45.92, 35.18, 34.26, 32.10, 31.03, 30.54, 29.22, 28.87, 28.70, 25.96. FT-IR (KBr) 3600–3100, 3100–3000, 3000–2800, 1732, 1723, 1716, 1680–1620, 1415, 1250–1150, 1095 $cm^{-1}$.

Example 6

Preparation of (R*, S*)-methyl (±)-α-hydroxy-β-[(2-(methoxycarbonyl)ethyl)thio]-2-(8-phenyloctyl)benzenepropanoate The product of Example 5 (100 mg) was treated with diazomethane/ether to afford the title compound: IR (neat) 3450, 3200–3000, 3000–2800, 1741, 1603, 1495, 1452, 1437, 1359, 1247, 1217, 1172, 1113, 1098, 750, 700 $cm^{-1}$; $^1H$ NMR (CDCl$_3$, 400 MHz). δ 7.61 (d, 1H), 7.29–7.12 (m, 8H), 4.61–4.58 (m, 1H), 4.54 (d, 1H), 3.65 (s, 3H), 3.64 (s, 3H), 3.13 (d, 1H), 2.80–2.51 (m, 8H), 1.61–1.55 (m, 4H), 1.38–1.34 (m, 8H); $^{13}C$ NMR (CDCl$_3$, 100 MHz) δ 172.49, 172.17, 142.93, 140.72, 134.82, 129.59, 128.86, 128.47, 138.31, 127.91, 126.25, 125.66, 73.23, 52.43, 51.89, 48.07, 36.05, 34.40, 32.60, 31.57, 31.35, 29.85, 29.56, 29.38, 26.81. HPLC RT 5.3 min (desired regioisomer, α-hydroxy-β-sulfido-propionate), 4.9 min (undesired regioisomer, α-sulfido-β-hydroxy-propionate) (Waters Nova-Pak® C-18; water: acetonitrile: acetic acid, 80:20:0.1; UV detection at 215 nm). HPLC indicates a ratio of 79:1 in favor of the desired α-hydroxy-β-sulfido-propionate regioisomer.

Example 7

Preparation of (R*, S*)-(±)-β-[(2-carboxyethyl)thio]-α-hydroxy-2-(8-phenyloctyl)benzenepropanoic acid To a solution of trans-3-[2-(8-phenyloctyl)phenyl]oxiranecarboxylic acid (780.0 g, 2.2 mol) in tetrahydrofuran (5.9 L) at ambient temperature was added lithium hydroxide monohydrate (119.4 g, 2.8 mol). The reaction mixture was stirred for 1 hour, then cooled to 0°–5° C. Methyl 3-mercaptopropionate (333.8 g, 2.7 mol) was added. The mixture was stirred for 1–2 hours at 0°–5° C. Aqueous sodium hydroxide was then added (1.3 L of a 2.5N solution), and the reaction mixture stirred for an additional 30 minutes. The pH of the solution was adjusted to 1.2–1.4 by addition of 6N aqueous hydrochloric acid. After vigorous stirring, the mixture was allowed to settle, and the layers were separated. The organic phase was washed with aqueous sodium chloride, then concentrated to a viscous oil. This residue was redissolved in ethyl acetate, and concentrated again in order to remove water. The product was then precipitated from a mixture of ethyl acetate and hexanes. After cooling below 10° C., the product was isolated by filtration, washed with hexanes, and dried in vacuo. This afforded 1024.0 g of the title compound as a white powder: m.p. 91°–92° C.; $^1H$ NMR (DMSO-$d_6$, 360 MHz) δ 12.41 (s, 2H), 7.50 (s, 1H), 7.29–7.10 (m, 8H), 5.73 (s, 1H), 4.35 (s, 2H), 2.70–2.51 (m, 6H), 2.50–2.33 (m, 2H), 1.56 (m, 4H), 1.31 (s, 8H); $^{13}C$ NMR (DMSO-$d_6$, 90 MHz) δ 173.56, 172.73, 142.32, 140.68, 136.76, 128.93, 128.62, 128.24, 128.18, 126.74, 125.54, 73.01, 45.92, 35.18, 34.26, 32.10, 31.03, 30.54, 29.22, 28.87, 28.70, 25.96; FT-IR (KBr) 3600–3100, 3100–3000, 3000–2800, 1732, 1723, 1716, 1680–1620, 1415, 1250, 1150, 1095 $cm^{-1}$. Anal. Calcd for $C_{26}H_{34}O_5S$: C, 68.09; H, 7.47; S, 6.99. Found: C, 67.93; H, 7.28; S, 7.24.

After conversion of the diacid to the corresponding methyl diester according to the procedure of Example 6, HPLC analysis of the diester indicated a ratio of 36:1 in favor of the desired α-hydroxy-β-sulfido-propionate regioisomer.

Example 8

Preparation of (R*, S*)-methyl (±)-α-hydroxy-β-[(2-(methoxycarbonyl)ethyl)thio)-2-(8-phenyloctyl)benzenepropanoate To a cooled (–5° C.) mixture of 60% sodium hydride (0.56 g, 14.0 mmol) and tetrahydrofuran (15 mL) was added methyl 3-mercaptopropionate (1.55 mL, 14.0 mmol). To this mixture was added a solution of the compound of Example 1 (2.35 g, 6.67 mmol) in tetrahydrofuran (15 mL). The mixture was stirred at 0° C. until the reaction was complete by HPLC. The reaction mixture was quenched with water and acidified with hydrochloric acid. The layers were separated. The organic layer was washed with aqueous sodium chloride and concentrated in vacuo. The residue was treated with diazomethane/ether to afford the titled compound: $^1H$ NMR (CDCl$_3$, 400 MHz) δ 7.62–7.59 (m, 1H), 7.29–7.12 (m, 8H), 4.61–4.58 (m, 1H), 4.54 (d, 1H), 3.66 (s, 3H), 3.64 (s, 3H), 3.08 (d, 1H), 2.81–2.52 (m, 8H), 1.61–1.55 (m ,4H), 1.34 (s, 8H); HPLC RT 5.3 min (Waters Nova-Pak® C-18; water:acetonitrile:acetic acid, 80:20:0.1; UV detection at 215 nm).

Example 9

[R-(R*, S*)]-β-[(2-carboxyethyl)thio]-α-hydroxy-2-
(8-phenyloctyl)benzenepropanoic acid, bis
ammonium salt, monohydrate To a mixture of 2R-trans-3-[2-(8-phenyloctyl)phenyl] oxiranecarboxylic acid lithium salt (1.162 kg, 3.24 mol), dry tetrahydrofuran (8.13 L) and methyl-3-mercaptopropionate (448.5 mL, 4.05 mol) at 5° C. was added 25% sodium methoxide/methanol solution (34.9 g, 0.16 mol) in one portion. The resulting mixture was stirred at 5°–10° C. for approximately 4 h. To the solution was added 2.5N aqueous Sodium hydroxide (2.9 L, 7.25 mol) over a 15 min period, allowing the temperature to rise to 25° C. After 30–45 min, the pH of the reaction solution was adjusted to 2.5 with 6N aqueous hydrochloric acid. The phases were separated, and the aqueous layer extracted with ethyl acetate (1×2 L). The initial tetrahydrofuran extract was washed with 10% aqueous sodium chloride and concentrated in vacuo to a viscous oil. The ethyl acetate back extract was washed with the spent sodium chloride wash then added to the tetrahydrofuran concentrate. Reconcentration afforded the crude diacid as a viscous yellow-orange oil. The crude oil was redissolved in anhydrous acetone (12.5 L) and the pH was slowly adjusted to 6.5 with concentrated ammonium hydroxide. The product was allowed to crystallize for 30 min, and then the pH was adjusted to 8.4 with additional concentrated ammonium hydroxide. After cooling the mixture, the product was isolated by filtration, washed, and then dried in vacuo to afford a white powder (1.444 kg).

The crude bis ammonium salt was suspended in anhydrous acetone (7.06 L), and deionized water was added until the salt completely dissolved. The solution was filtered, then additional anhydrous acetone (4.3 L) was added over a 30 min period. The product was allowed to crystallize at room temperature for 60 min and at 0° C. for 15 h, filtered, washed, and dried in vacuo to afford a white crystalline solid (1.145 kg, 69.7%): mp 91°–96° C.; Karl Fischer Analysis= 3.62%; $[\alpha]_D$ –47.6° (C 1.0, $H_2O$); $^1H$ NMR (DMSO-$d_6$, 400 MHz) δ 7.63 (m, 1H), 7.28–6.98 (m, 8H), 4.49 (d, 1H, J=3.3 Hz), 3.95 (d, 1H, J=3.3 Hz), 2.91–2.84 (m, 1H), 2.65–2.41 (m, 5H), 2.30–2.14 (m, 2H), 1.54 (m, 4H), 1.30 (s, 8H); $^{13}C$ NMR (DMSO-$d_6$, 67.8 MHz) δ 174.24 (2 carbons), 142.26, 140.46, 137.98, 130.07, 128.45, 128.25, 128.20, 125.98, 125.55, 124.77, 73.52, 46.36, 36.77, 35.19, 32.37, 31.10, 30.61, 29.29, 29.00, 28.94, 28.74, 27.41; FT-IR (Far) 3600–2800, 3100–3000, 3000–2800, 1567, 1387, 1097, 767, 749, 698 $cm^{-1}$; Anal. Calcd for $C_{26}H_{40}N_2O_5S \cdot H_2O$: C, 61.15; H, 8.27; N, 5.49; S, 6.28. Found: C, 61.19; H,. 8.36; N, 5.52; S, 6.28.

Example 10

[R-(R*, S*)]-β-[(2-carboxyethyl)thio]-α-hydroxy-2-
(8-phenyloctyl)benzenepropanoic acid, bis
ammonium salt, monohydrate To a mixture of sodium hydride (1.23 g, 30.66 mmol, 60% oil dispersion) in methylene chloride (36 mL) at –10° C., was added methyl-3-mercaptopropionate (3.40 mL, 30.66 mmol) over a 5 min period. The mixture was stirred at –10° to –5° C. for 40 min. Meanwhile, a mixture of 2R-trans-3-[2-(8-phenyloctyl)phenyl]oxiranecarboxylic acid lithium salt (10.0 g, 27.87 mmol) and tetrahydrofuran (70 mL) was stirred at reflux for 40 min, cooled to 5°–10° C. and then added to the sodium thiolate mixture at –10° to –5° C. over a 5 min period. The resulting mixture was stirred at –5° C. for approximately 45 min. To this solution was added 1N aqueous sodium hydroxide (25 mL, 25 mmol), while maintaining the temperature below 15° C. After approximately 60 min, the pH of the reaction solution was adjusted to 2.5 with 25% aqueous hydrochloric acid. The phases were separated and the aqueous phase extracted with methylene chloride (1×25 ml). The combined extracts were washed with 10% aqueous sodium chloride, then concentrated in vacuo to afford a viscous oil (14.6 g).

The crude oil was redissolved in acetone (100 mL) and the pH was slowly adjusted to 6.4 with concentrated ammonium hydroxide. The product was allowed to precipitate for 15 min, and then the pH was adjusted to 8.4 with additional concentrated ammonium hydroxide. After cooling the mixture to 0° C., the product was isolated by filtration, washed, and dried in vacuo to afford a white powder (12.37 g).

The crude bis ammonium salt was suspended in anhydrous acetone (100 mL), and deionized water was added until the salt completely dissolved. The solution was seeded and slowly cooled to 0° C. The product was filtered, washed and dried in vacuo to afford a white crystalline solid (9.80 g, 68.0%): $^1H$ NMR (DMSO-$d_6$, 400 MHz) δ 7.65–7.63 (m, 1H), 7.28–6.98 (m, 8H), 4.50 (d, 1H, J=3.1 Hz), 3.93 (d, 1H, J=3.1 Hz), 2.92–2.85 (m, 1H), 2.65–2.40 (m, 6H), 2.34–2.08 (m, 2H), 1.55–1.52 (m, 4H), 1.30 (s, 8H).

Example 11

[R-(R*, S*)]-β-[(2-carboxyethyl)thio]-α-hydroxy-2-
(8-phenyloctyl)benzenepropanoic acid, bis
ammonium salt, monohydrate To a solution of methyl-3-mercaptopropionate (48.2 mL, 0.43 mol) in tetrahydrofuran (450 mL) at –10° to –15° C. was added n-BuLi in hexanes (2.5M, 174 mL, 0.43 mol) over a 15 min period, maintaining the reaction temperature below –5° C. The solution was then stirred at –15° C. for 45 min. Meanwhile, a mixture of 2R-trans-3-[2-(8phenyloctyl) phenyl]oxiranecarboxylic acid lithium salt ( 125.0 g, 0.35 mol) and tetrahydrofuran (875 mL) was stirred at reflux for 45 min, cooled to 5° C. and then added to the lithium thiolate solution at –15° C. over a 30 min period. The resulting solution was stirred at –5° C. for approximately 45 min. To the solution was added aqueous sodium hydroxide (1N, 312.5 mL) over a 5 min period, allowing the temperature to rise to room temperature. After 60 min, the pH of the reaction solution was adjusted to 2.0–2.5 with 25% aqueous hydrochloric acid. The phases were separated and the aqueous phase extracted with ethyl acetate (1×250 ml). The combined extracts were washed with 10% aqueous sodium chloride then concentrated in vacuo to afford a viscous oil (203.08 g). The crude oil was redissolved in anhydrous acetone (1300 mL) and the pH slowly adjusted to 6.7–6.9 with concentrated ammonium hydroxide. The product was allowed to precipitate for 30 min and the pH was then adjusted to 8.2 with additional concentrated ammonium hydroxide. After cooling the mixture to 0° C., the product was isolated by filtration, washed, and dried in vacuo to afford a white powder (143.2 g).

The crude bis ammonium salt was suspended in anhydrous acetone (812 mL), and deionized water was added until the salt completely dissolved. The solution was filtered, seeded, and treated with additional acetone (300 mL). The product was allowed to slowly crystallize at room temperature, cooled to 0° C., filtered, washed, and dried in vacuo to afford a white crystalline solid (120.5 g, 69.1%): $^1H$ NMR (DMSO-$d_6$, 400 MHz) δ 7.65–7.63 (m, 1H), 7.28–6.98 (m, 8H), 4.50 (d, 1H, J=3.1 Hz), 3.93 (d, 1H, J=3.2 Hz), 2.92–2.85 (m, 1H), 2.65–2.40 (m, 6H), 2.33–2.17 (m, 2H), 1.55–1.52 (m, 4H), 1.30 (s, 8H).

Example 12

[R-(R*, S*)]-β-[(4-carboxyphenyl)thio]-α-hydroxy-2-(8-phenyloctyl)benzenepropanoic acid To a stirred solution of 2R-trans-3-[2-(8-phenyloctyl)phenyl]oxiranecarboxylic acid lithium salt (1.16 g, 3.24 mmol) and methyl 4-mercaptobenzoate (0.672 g, 4.0 mmol) in dry tetrahydrofuran (15 mL) at 5° C. is added 25% sodium methoxide/methanol solution (0.74 g, 3.24 mmol). After stirring for approximately 6 h at 5°–10° C., 2.5N aqueous sodium hydroxide (3.24 mL, 8.0 mmol) is added, the reaction is stirred an additional 2 h, and the reaction solution is diluted with water (20 mL) and adjusted to pH 2.5 with 3N aqueous hydrochloric acid. The reaction mixture is extracted with ethyl acetate (2×20 mL), the organic extracts are washed with brine, and dried over magnesium sulfate. Filtration and evaporation of the solvent yields the titled compound.

Example 13

[R-(R*, S*)]-methyl β-[(4-methoxybenzyl)thio]-α-hydroxy-2-(8-phenyloctyl)benzenepropanoate a) [R-(R*, S*)]-β-[(4-methoxybenzyl)thio]-α-hydroxy-2-(8-phenyloctyl)benzenepropanoic acid.

To a stirred solution of 2R-trans-3-[2-(8-phenyloctyl)phenyl]oxiranecarboxylic acid lithium salt (1.16 g, 3.24 mmol) and 4-methoxybenzyl mercaptan (0.616 g, 4.0 mmol) in dry tetrahydrofuran (15 mL) at 5° C. is added 25% sodium methoxide/methanol solution (0.74 g, 3.24 mmol). After stirring for approximately 6 h at 5°–10° C., the reaction solution is diluted with water (20 mL) and adjusted to pH 2.5 with 3N aqueous hydrochloric acid. The reaction mixture is extracted with ethyl acetate (2×20 mL), the organic extracts are washed with brine, and dried over magnesium sulfate. Filtration and evaporation of the solvent yields the titled compound.

b) [R-(R*, S*)]-methyl β-[(4-methoxybenzyl)thio]-α-hydroxy-2-(8-phenyloctyl)benzenepropanoate.

The product of Example 13a is treated with an excess of diazomethane/ether to afford the titled compound.

Many variations of these examples will be apparent one skilled in the art and this invention is not limited to these examples, but includes all variations encompassed by the claims which follow.

What is claimed is:

1. A process for preparing a compound of the formula:

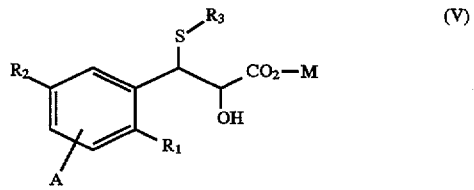

wherein:

$R_1$ is $(L)_a$—$(CH_2)_b$—$(T)_c$—B;

a is 0 or 1;

b is 3 to 14;

c is 0 or 1;

L and T are independently sulfur, oxygen, CH=CH, C≡C, or $CH_2$;

B is H, $C_{1-4}$alkyl, ethynyl, trifluoromethyl, isopropenyl, furanyl, thienyl, cyclohexyl or phenyl unsubstituted or monosubstituted by Br, Cl, $CF_3$, $C_{1-4}$alkoxy, $C_{1-4}$alkyl, methylthio or trifluoromethylthio;

M is H, Li, Na, K, $NH_4$ or an organic ammonium cation;

$R_2$ and A are independently selected from H, $CF_3$, $C_{1-4}$alkyl, $C_{1-4}$alkoxy, F, Cl, Br, I, OH, $NO_2$ or $NH_2$; or, when $R_1$ and A are H, $R_2$ is $(L)_a$—$(CH_2)_b$—$(T)_c$—B wherein a, b, c, L, T and B are as defined above;

$R_3$ is $(CH_2)_n CH(R_5)COR_6$, $CH(CO_2H)CH_2CO_2H$, $CH_2CH_2Z$,

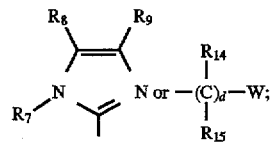

n is 0 to 6;

$R_5$ is hydrogen, amino, or $NHCOCH_2CH_2CH(NH_2)CO_2H$;

$R_6$ is hydroxy, amino, $NHCH_2CO_2H$ or $C_{1-6}$alkoxy;

Z is $SO_3H$, $SO_2NH_2$ or CN;

$R_7$ is hydrogen, $C_{1-4}$alkyl or $C_{3-4}$alkenyl;

$R_8$ is hydrogen, $C_{1-4}$alkyl, carboxyl, carboxamido, or $(CH_2)_p CO_2R_{12}$, wherein p is 1 or 2 and $R_{12}$ is $C_{1-6}$alkyl or hydrogen when $R_7$ and $R_9$ are hydrogen or $C_{1-4}$alkyl;

$R_9$ is hydrogen, $C_{1-4}$alkyl, or $(CH_2)_p CO_2R_{13}$, wherein p is 1 or 2 and $R_{13}$ is $C_{1-6}$alkyl or hydrogen, with the proviso that when n is 0, $R_5$ is hydrogen and further that $R_7$, $R_8$ and $R_9$ are not all hydrogen;

$R_{14}$ and $R_{15}$ are independently hydrogen or $C_{1-4}$alkyl at any point when d is not 0;

d is 0 to 6;

W is a six membered aryl or heteroaryl ring selected from phenyl, pyridyl or pyrimidyl, unsubstituted or substituted with G, E, or D; or a five membered heteroaryl ring selected from tetrazolyl, thiazolyl, triazolyl, thienyl, furyl, oxazolyl, thiadiazolyl, pyrolyl, imidazolyl or pyrazolyl, unsubstituted or substituted with G; or W is one of

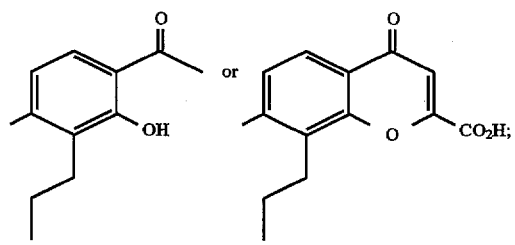

G is

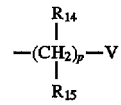

wherein $R_{14}$ and $R_{15}$ are independently hydrogen or $C_{1-4}$alkyl;

p is 0 to 6;

V is H, $C_{1-4}$alkyl, COR', $SO_3H$, $SO_2H$, $SO_2NH_2$, $COCH_2OH$, $CHOHCH_2OH$, or tetrazolyl, with R' as defined above;

R' is OH, $NH_2$, aryloxy or $C_{1-6}$alkoxy; and

E and D are independently selected from H, OH, F, Cl, Br, $CF_3$, $C_{1-4}$alkyl, $C_{1-4}$alkoxy, methylthio, trifluoromethylthio, $NO_2$, $NH_2$, $NHC_{1-4}$alkyl, or $C_{1-4}$alkylCO—, with any groups optionally protected;

which comprises, reacting a compound of the formula:

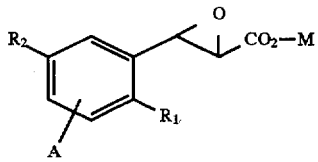 (VI)

wherein $R_1$, $R_2$, A and M are as defined above for formula (V), with a compound of the formula:

$R_3S—H$ wherein $R_3$ is as defined above for formula (V), with any reactive groups optionally protected, and a base.

2. A process according to claim 1 in which M is H or Li.

3. A process according to claim 1 in which A and $R_2$ are H.

4. A process according to claim 1 which is conducted in tetrahydrofuran.

5. A process according to claim 1 in which the base is an alkali metal alkoxide or hydroxide.

6. A process according to claim 1 which is conducted between −15° C. and 25° C.

7. A process according to claim 3 in which 1 to 2 equivalents of $R_3$—SH is used.

8. A process according to claim 3 in which $R_3$ is $CH_2CH_2COR_6$ or phenyl substituted with —COR', or 4-methoxybenzyl.

* * * * *